US008439034B2

(12) United States Patent
Decker et al.

(10) Patent No.: US 8,439,034 B2
(45) Date of Patent: May 14, 2013

(54) OXYGEN CONSERVING OXYGEN DELIVERY SYSTEM

(75) Inventors: Thomas D. Decker, Redmond, OR (US); Patrick L. McLaughlin, Redmond, OR (US)

(73) Assignee: IPG, LLC, Redmond, OR (US)

( * ) Notice: Subject to any disclaimer, the term of this patent is extended or adjusted under 35 U.S.C. 154(b) by 997 days.

(21) Appl. No.: 12/472,853

(22) Filed: May 27, 2009

(65) Prior Publication Data

US 2010/0300444 A1 Dec. 2, 2010

Related U.S. Application Data

(60) Provisional application No. 61/056,770, filed on May 28, 2008.

(51) Int. Cl.
*F16K 31/02* (2006.01)
*A61M 16/00* (2006.01)

(52) U.S. Cl.
USPC ............. 128/204.23; 128/204.21; 128/204.18

(58) Field of Classification Search . 128/204.18–205.24
See application file for complete search history.

(56) References Cited

U.S. PATENT DOCUMENTS

| 3,678,296 | A | * | 7/1972 | Day .............................. 327/15 |
|---|---|---|---|---|
| 4,057,205 | A | | 11/1977 | Vensel |
| 4,651,728 | A | | 3/1987 | Gupta et al. |
| 4,686,975 | A | | 8/1987 | Naimon et al. |
| 5,052,400 | A | | 10/1991 | Dietz |
| 5,134,886 | A | | 8/1992 | Ball |
| 5,195,528 | A | | 3/1993 | Hok |
| 5,492,129 | A | * | 2/1996 | Greenberger ................. 600/528 |
| 5,558,086 | A | | 9/1996 | Smith et al. |
| 5,603,315 | A | | 2/1997 | Sasso, Jr. |
| 5,697,364 | A | | 12/1997 | Chua et al. |
| 5,865,174 | A | | 2/1999 | Kloeppel |
| 6,213,955 | B1 | * | 4/2001 | Karakasoglu et al. ........ 600/529 |
| 6,220,244 | B1 | * | 4/2001 | McLaughlin ............ 128/204.23 |
| 6,418,793 | B1 | | 7/2002 | Pechoux et al. |
| 6,427,690 | B1 | | 8/2002 | McCombs et al. |
| 6,470,885 | B1 | | 10/2002 | Blue et al. |
| 6,532,958 | B1 | | 3/2003 | Buan et al. |
| 6,575,163 | B1 | | 6/2003 | Berthon-Jones |
| 6,712,876 | B2 | | 3/2004 | Cao et al. |
| 6,910,482 | B2 | | 6/2005 | Bliss et al. |
| 6,925,884 | B2 | | 8/2005 | Hegner et al. |
| 6,992,492 | B2 | | 1/2006 | Burdick et al. |
| 7,013,898 | B2 | | 3/2006 | Rashad et al. |
| 7,089,938 | B2 | | 8/2006 | Gale et al. |
| 2002/0038657 | A1 | * | 4/2002 | Yagi et al. ................ 128/204.23 |

(Continued)

*Primary Examiner* — Justine Yu
*Assistant Examiner* — Rachel Young
(74) *Attorney, Agent, or Firm* — Workman Nydegger

(57) ABSTRACT

The present invention extends to methods, systems, computer program products, and circuits for conserving oxygen during the delivery of oxygen to a user. Embodiments of the invention use a microphone to detect breathing sounds indicative of different portions of a breathing cycle. Sounds not related to the breathing cycle are filtered out of the signal. Using the breathing sounds, a microprocessor differentiates inspiration from other portions of the breathing cycle. When inspiration is detected, a valve is transitioned to permit the flow of oxygen from an oxygen source to a user to deliver an appropriate bolus of oxygen. The microprocessor can also detect fault conditions, such as, for example, apnea, failure to deliver a bolus of oxygen, and restrictions in the flow of oxygen from the oxygen source to a user.

21 Claims, 8 Drawing Sheets

U.S. PATENT DOCUMENTS

| | | | |
|---|---|---|---|
| 2004/0035422 A1* | 2/2004 | Truitt et al. | 128/204.18 |
| 2006/0118115 A1 | 6/2006 | Cannon | |
| 2006/0180149 A1* | 8/2006 | Matarasso | 128/204.18 |
| 2008/0000480 A1 | 1/2008 | Cannon | |
| 2008/0035150 A1 | 2/2008 | Rittner et al. | |
| 2008/0053541 A1 | 3/2008 | Meckes et al. | |
| 2008/0078392 A1 | 4/2008 | Pelletier et al. | |
| 2008/0282880 A1* | 11/2008 | Bliss et al. | 95/11 |
| 2009/0056708 A1* | 3/2009 | Stenzler et al. | 128/200.14 |

\* cited by examiner

OXYGEN CONSERVING OXYGEN DELIVERY SYSTEM

CROSS-REFERENCE TO RELATED APPLICATIONS

The present application claims priority to U.S. Provisional Patent Application No. 61/056,770, filed May 28, 2008, and titled "OXYGEN CONSERVING DEVICE", which is herein incorporated by reference in its entirety.

BACKGROUND OF THE INVENTION

The state of the art in oxygen therapy is replete with systems that attempt to conserve oxygen being supplied to a user. The need to conserve oxygen is a result of the understanding that continuous, long term oxygen therapy is expensive because of the large quantities of oxygen that need to be provided to a user. For example, oxygen conservation in aviation applications saves both space and weight.

Less sophisticated oxygen therapy systems provide oxygen at a continuous rate without interruption. The result is that all oxygen supplied to the user during exhalation is wasted. The wasted oxygen can be substantial considering that approximately two thirds of the respiratory cycle is spent in exhalation. Furthermore, these systems do not adjust for rates or depth of inspiration by the user. These factors, combined with the fact that the oxygen therapy is generally being conducted using a mobile oxygen container, demonstrate the need for more prudent oxygen conservation.

As such, more sophisticated systems have been developed which are designed to deliver oxygen only during user inspiration. However, the methods and apparatus for delivering oxygen only during user inspiration met with varying degrees of success.

One method for accomplishing conservation during oxygen therapy is to provide pulsed oxygen delivery to the patient according to some control logic. The control logic can be based upon any number of factors, such as, for example, a prescription, a Federal Aviation Administration ("FAA") mandated altitude compensated gas flow rate, breathing characteristics of the user, etc. For example, studies support the observation that the first portion of inspiration is the most effective time for oxygen delivery, with the last portion of the user's inspiration not actually providing oxygen to the secondary respiratory system (i.e. the blood stream).

Some systems provide oxygen on demand, where the system is responsive to a patient's breathing. However, these systems have numerous drawbacks which prevent them from serving all the functions of an acceptable oxygen conservation device. These drawbacks include, but are not limited to, a failure to adequately adapt to breathing depth (force) of the person using the system. They also fail to take into account changes that occur due to variations in altitude of the user. They also fail to compensate for changes in battery strength, and fail to adequately conserve battery power.

Other electronic oxygen conserving devices use various methods for sensing the respiration event so that a valve can be triggered to allow oxygen to flow to the user. The sensor to detect breathing events can range from an off-the-shelf low-pressure sensor to a discreetly assembled membrane material based sensor. Many off-the-shelf low-pressure sensors require a second valve to remove the sensor from the pneumatic path to protect it from the high-pressure burst that occurs when oxygen is flowing.

Membrane material based sensors contain a thin flexible membrane that moves in relation to the minute pressure changes caused during breathing. Many of these membrane type sensors are able to handle the pressure of the valve passing the oxygen, but can be expensive to manufacture and then calibrate for use. Electrical signals, corresponding to breathing pressures, are derived from the movements resulting from the minute pressure changes when breathing. The signal from any sensor type is processed so that a valve can be opened at the opportune time.

Electronic Demand Pulsed-Dose oxygen delivery systems deliver oxygen to a user (e.g., a human patient) by detecting the user's (patient's) inspiratory effort and providing gas flow during the initial portion of inspiration. This method reduces the amount of oxygen needed by approximately 50 to 85% (compared to continuous flow) and significantly reduces the cost, the supplies needed, and the limitations on mobility caused by a limited oxygen supply.

As a user initiates a breath, for example, through a cannula tip or mask, the sensor detects the inhalation. In response to detecting inhalation, a solenoid valve opens, and a burst of oxygen is rapidly delivered to the user. The size of the burst or flow can vary. The pulsed-dose system takes the place of a flowmeter during oxygen therapy and is attached to an oxygen source. In most devices, an operator can select the gas flow and the mode of operation (either pulse or continuous flow). A battery-powered fluidic valve is attached to a gaseous or liquid oxygen supply to operate the system.

Other methods used to further reduce oxygen usage when using the pulse-demand system include: reducing the amount of oxygen delivered to the patient during each oxygen pulse and/or to deliver an oxygen pulse only on the second or third breath instead of every breath. In addition, the amount of oxygen in the oxygen pulse can change with the flow setting. Increasing the flow setting can be used to deliver pulses with more oxygen and lowering the flow setting can be used to deliver pulses with less oxygen.

In aviation applications, oxygen distribution can also be delayed until an altitude threshold has been reached.

Potential problems encountered when using the pulse-demand system include either no oxygen flow from the device or decreased oxygen saturation in the patient. If no oxygen flow is detected, then possible causes may include a depletion of the gas supply, an obstruction or disconnection of the connecting tubing, or an inability of the device to detect the patient's effort to breath. If the device cannot detect the patient's inspiratory effort, the sensitivity will need to be increased or the nasal cannula will need to be repositioned in the nares.

A decrease in the patient's oxygen saturation should always be a cause for alarm and may indicate a change in the patient's medical status, tachypnea, or a failure in the device. In any case, a backup system should be available in order to verify whether the problem is with the device or with the patient.

Additionally, pulsed-dose systems are typically costly and have increased complexity. The increased complexity results in a variety of technical problems. For example, pulsed-dose systems may fail to increase oxygen dosage during periods of increased need, such as, for example, exercise, stress, illness, etc. They also have complicated setup procedure which can result in disconnections, improper placement of the device, possible device failures, etc.

BRIEF SUMMARY

The present invention extends to methods, systems, computer program products, and circuits for conserving oxygen during the delivery of oxygen to a user. In some embodiments, an oxygen delivery system operates to regulate a flow of oxygen during an inspiration event of a respiratory cycle. The system includes an oxygen source, an electronically controlled valve, a valve controller, a microphone, an oxygen delivery component (e.g., a cannula or facemask), a filter, and a microprocessor. A first portion of conduit pneumatically couples the oxygen source first pneumatic port of the electronically controlled valve. A second portion of conduit couples a second port of the electronically controlled valve to the oxygen delivery component and to a microphone.

The electronically controlled valve has at least an open setting and a closed setting. The open setting permits the flow of oxygen from the first port to the second port. The closed setting prevents the flow of oxygen from the first port to the second port.

The microphone is configured with a diaphragm and a transducer. User breathing at the oxygen delivery component as well as sound and pressure changes in the second portion of conduit influence movement of the diaphragm. Movement of the diaphragm results in a microphone signal having a sound component, a pneumatically induced noise component, and a user breathing component. The transducer is configured to convert diaphragm movements into microphone output electrical signals.

A microcontroller is electrically connected to the microphone. Generally, the microcontroller regulates operation of the oxygen delivery system so as to conserve oxygen.

The microcontroller is also electrically connected to the valve controller via an electrical connection. The valve controller controls the electronically controlled valve. The valve control can transition the electronically controlled valve from the closed setting to the open setting, can maintained the electronically controlled valve in the open setting, can transition the electronically controlled valve from an open setting to a closed setting, and can maintain electronically controlled valve in the closed setting.

The microcontroller is further configured to receive output electrical signals from the microphone The microcontroller filters portions of the sound component and portions of the pneumatically induced noise component from received microphone output electrical signals. Filtering leaves primarily the breathing component of the microphone output electrical signals as a filtered output signal.

The microcontroller is also configured to determine when a filtered output signal is indicative of an inspiration event. Accordingly, the electronically controlled valve can be transitioned to the open setting to deliver a specified bolus of oxygen. The microcontroller is also configured to determine when delivery of the specified bolus of oxygen is complete. Accordingly, the electronically controlled valve can be transitioned to the closed setting.

Other embodiments of the invention include a method for supplying oxygen to a user's respiratory system during a user's respiration cycle that includes inspiration. Movement of a microphone diaphragm is detected. One or more of sound, pressure changes, and user breathing in a conduit influence diaphragm movement. Movement of the diaphragm generates a microphone signal having a sound component, a pneumatically induced noise component, and a user breathing component.

The microphone detected movement is converted to an electrical signal collectively representing the sound component, the pneumatically induced noise component, and the user breathing component. Portions of the sound component and pneumatically induced noise component are filtered from the electrical signal. Filtering leaves primarily the breathing component of the electrical signal as a filtered output signal. The filtered output signal is processed to detect what portion of the respiration cycle the user is in.

Based on the detected portion of the respiration cycle, oxygen is selectively permitted to flow from an oxygen source to an oxygen delivery device. Selectively permitting the flow of oxygen includes permitting oxygen flow from the oxygen source to the oxygen delivery device to deliver an appropriate bolus of oxygen to the user in response to detecting an inspiration portion of the breathing cycle. Selectively permitting the flow of oxygen also includes preventing oxygen flow from the oxygen source to the oxygen delivery device after the appropriate bolus of oxygen is delivered and until an inspiration portion of the breathing cycle is again detected so as to conserve oxygen.

This summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages of the invention will be set forth in the description which follows, and in part will be obvious from the description, or may be learned by the practice of the invention. The features and advantages of the invention may be realized and obtained by means of the instruments and combinations particularly pointed out in the appended claims. These and other features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION

Figure 1A:
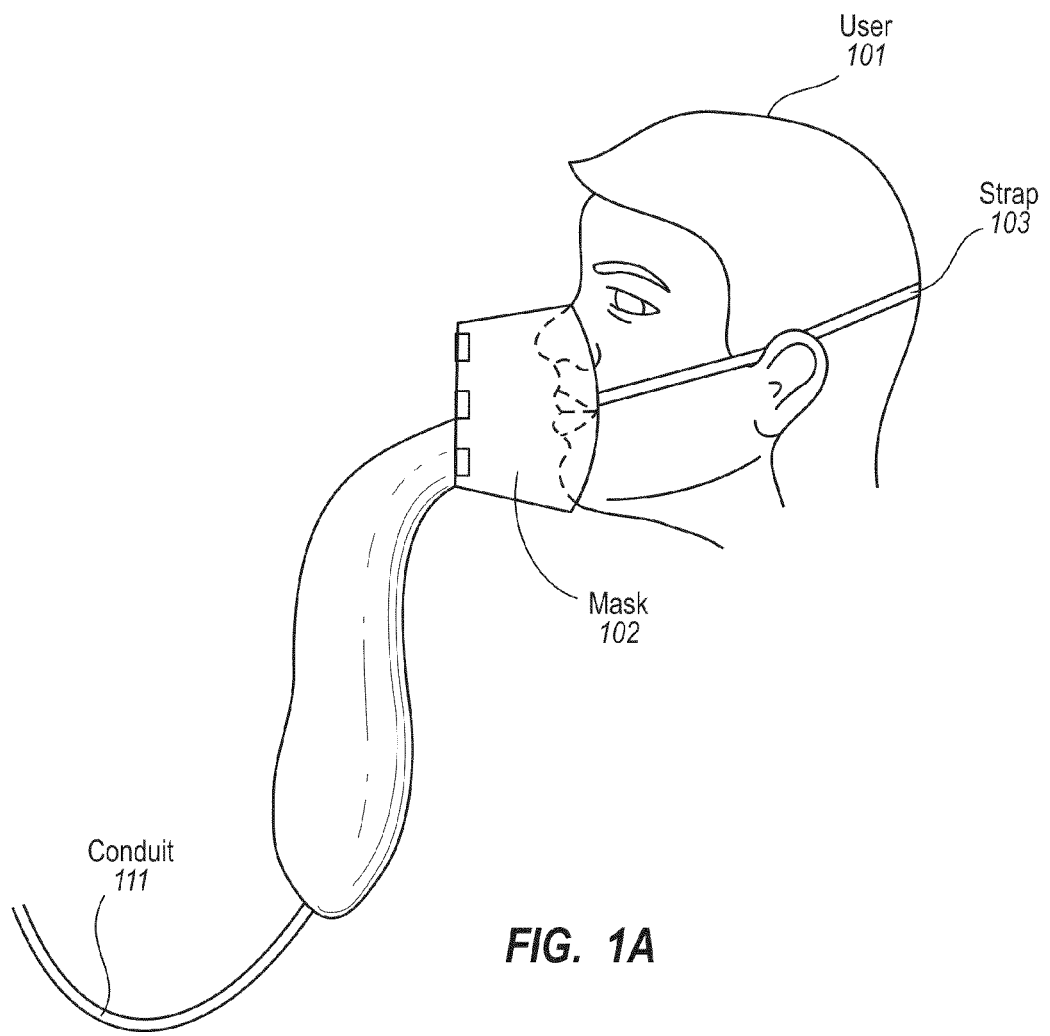
FIGS. 1A-1C illustrate different oxygen delivery components for delivering oxygen to a user.

The present invention extends to methods, systems, computer program products, and circuits for conserving oxygen during the delivery of oxygen to a user. In some embodiments, an oxygen delivery system operates to regulate a flow of oxygen during an inspiration event of a respiratory cycle. The system includes an oxygen source, an electronically controlled valve, a valve controller, a microphone, an oxygen delivery component (e.g., a cannula or facemask), a filter, and a microprocessor. A first portion of conduit pneumatically couples the oxygen source first pneumatic port of the electronically controlled valve. A second portion of conduit couples a second port of the electronically controlled valve to the oxygen delivery component and to a microphone.

The electronically controlled valve has at least an open setting and a closed setting. The open setting permits the flow of oxygen from the first port to the second port. The closed setting prevents the flow of oxygen from the first port to the second port.

The microphone is configured with a diaphragm and a transducer. User breathing at the oxygen delivery component as well as sound and pressure changes in the second portion of conduit influence movement of the diaphragm. Movement of the diaphragm results in a microphone signal having a sound component, a pneumatically induced noise component, and a user breathing component. The transducer is configured to convert diaphragm movements into microphone output electrical signals.

A microcontroller is electrically connected to the microphone. Generally, the microcontroller regulates operation of the oxygen delivery system so as to conserve oxygen.

The microcontroller is also electrically connected to the valve controller via an electrical connection. The valve controller controls the electronically controlled valve. The valve control can transition the electronically controlled valve from the closed setting to the open setting, can maintained the electronically controlled valve in the open setting, can transition the electronically controlled valve from an open setting to a closed setting, and can maintain electronically controlled valve in the closed setting.

The microcontroller is further configured to receive output electrical signals from the microphone The microcontroller filters portions of the sound component and portions of the pneumatically induced noise component from received microphone output electrical signals. Filtering leaves primarily the breathing component of the microphone output electrical signals as a filtered output signal.

The microcontroller is also configured to determine when a filtered output signal is indicative of an inspiration event. Accordingly, the electronically controlled valve can be transitioned to the open setting to deliver a specified bolus of oxygen. The microcontroller is also configured to determine when delivery of the specified bolus of oxygen is complete. Accordingly, the electronically controlled valve can be transitioned to the closed setting.

Other embodiments of the invention include a method for supplying oxygen to a user's respiratory system during a user's respiration cycle that includes inspiration. Movement of a microphone diaphragm is detected. One or more of sound, pressure changes, and user breathing in a conduit influence diaphragm movement. Movement of the diaphragm generates a microphone signal having a sound component, a pneumatically induced noise component, and a user breathing component.

The microphone detected movement is converted to an electrical signal collectively representing the sound component, the pneumatically induced noise component, and the user breathing component. Portions of the sound component and pneumatically induced noise component are filtered from the electrical signal. Filtering leaves primarily the breathing component of the electrical signal as a filtered output signal. The filtered output signal is processed to detect what portion of the respiration cycle the user is in.

Based on the detected portion of the respiration cycle, oxygen is selectively permitted to flow from an oxygen source to an oxygen delivery device. Selectively permitting the flow of oxygen includes permitting oxygen flow from the oxygen source to the oxygen delivery device to deliver an appropriate bolus of oxygen to the user in response to detecting an inspiration portion of the breathing cycle. Selectively permitting the flow of oxygen also includes preventing oxygen flow from the oxygen source to the oxygen delivery device after the appropriate bolus of oxygen is delivered and until an inspiration portion of the breathing cycle is again detected so as to conserve oxygen.

Accordingly, embodiments of invention generally relate to electronic pulse-type oxygen delivery devices. The electronic pulse-type oxygen delivery devices can be used for variety of different applications, including aviation and medical use. More particularly, the embodiments improve manufacturability and reduce the cost of sensors used to monitor breathing events. Embodiments of the invention can be used to reduce oxygen consumption while maintaining adequate alveolar gas exchange of a user.

DEFINITIONS

Within this description and following claims, "inspiration" and "inhalation" are defined as drawing air into the lungs during breathing.

Within this description and following claims, "expiration" and "exhalation" are defined as emission of air from the lungs during breathing.

Within this description and following claims, a "positive artifact" is defined as a burst of positive pressure into an oxygen delivery system. It can be caused by an oxygen burst, a user expiring, or outlet-side tubing getting tossed or shaken. The drop from this positive pressure back to a lower pressure can appear to the system like the inspiration portion of a breathing cycle. Positive artifacts must be detected to avoid false triggering.

Within this description and following claims, a "false trigger" is defined as triggering upon a negative-pressure waveform from something other than the inspiration portion of a breathing cycle.

Within this description and following claims, a "breathing cycle" or "envelope" is defined as starting at inspiration, then possibly a rest period, next expiration, and then another possible rest period.

Within this description and the following claims, a "transducer" is defined as a device, for example, electrical, electronic, electromechanical, electromagnetic, photonic, or photovoltaic that converts one type of energy or physical attribute to another type of energy or physical attribute for various purposes, including measurement or information transfer. For example, a pressure sensor can convert pressure energy to electrical energy.

Within this description and following claims, a "microphone" is defined as an acoustic(sound)-to-electric transducer or sensor that converts sound energy into an electrical signal. A microphone can include an acoustical port for detecting sound and an electrical port for outputting an electrical signal.

Within this description and the following claims, a "diaphragm" (is defined a thin, semi-rigid membrane. Air vibrations (sound) causing the diaphragm to move are converting into electrical signals by a transducer. A microphone can include a diaphragm.

Within this description and following claims, "depth of inspiration" is defined as the volume of gaseous mixture a person has inspired in one respiration cycle. This volume will increase or decrease as the person's needs change from breath to breath. Typical factors that cause an increase in person's depth of inspiration may include an increase in physical exertion.

Within this description and following claims, "respiration rate" is defined as the number of respiration cycles a person has completed in a given period of time. This number will increase or decrease as the person's needs change from breath to breath. Typical factors that cause an increase in person's respiration rate may include an increase in physical exertion.

Oxygen Delivery Components

A variety of different oxygen delivery components can be used by a user to receive oxygen from an oxygen delivery system. Oxygen delivery components can include a variety of different types of cannulas and masks. For example, FIG. 1A depicts mask 102. Mask 102 fully covers the nose and mouth of user 101. Strap 103 secures mask 102 to the head of user 101. Conduit 111 can be connected to an oxygen supply such that oxygen can, when appropriate, flow into mask 102 for inspiration by user 101.

Figure 1B:
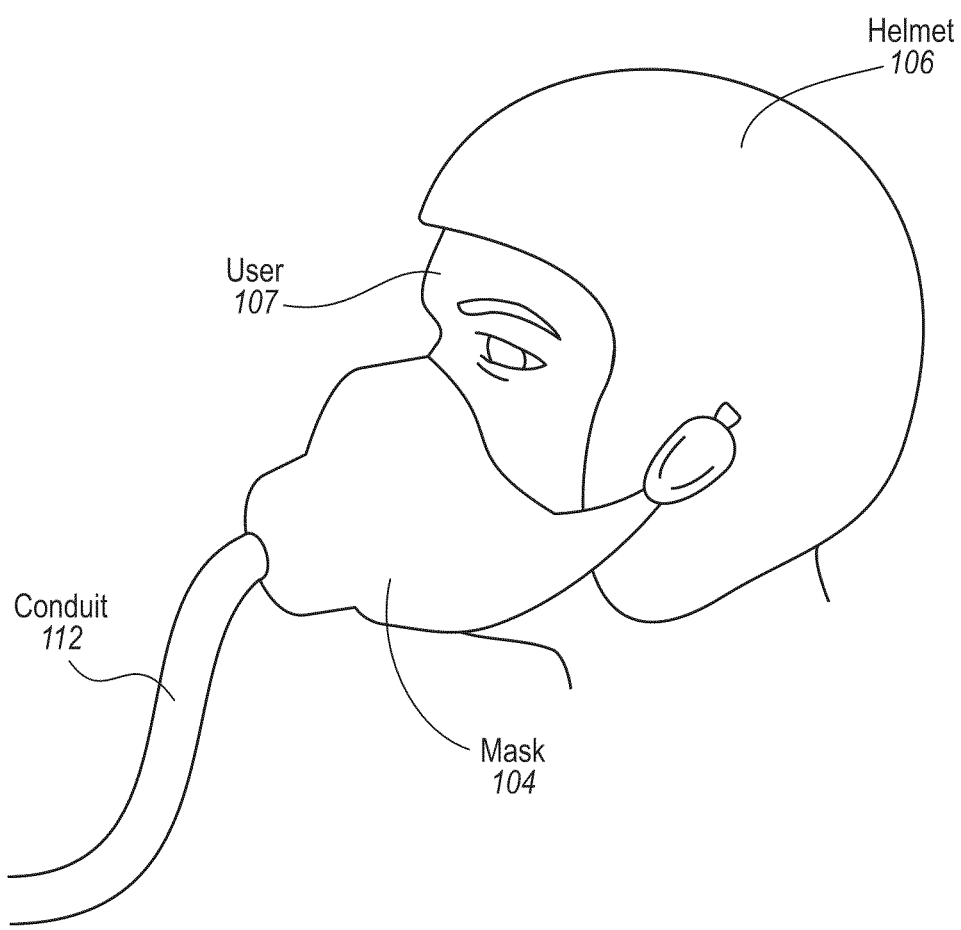

Other configurations of masks can also be used. FIG. 1B depicts mask 104. Mask 104 fully covers the nose and mouth of user 107. Mask 104 is connected to helmet 106, securing mask 104 to the head of user 107. Conduit 112 can be connected to an oxygen supply such that oxygen can, when appropriate, flow into mask 104 for inspiration by user 107.

Figure 1C:
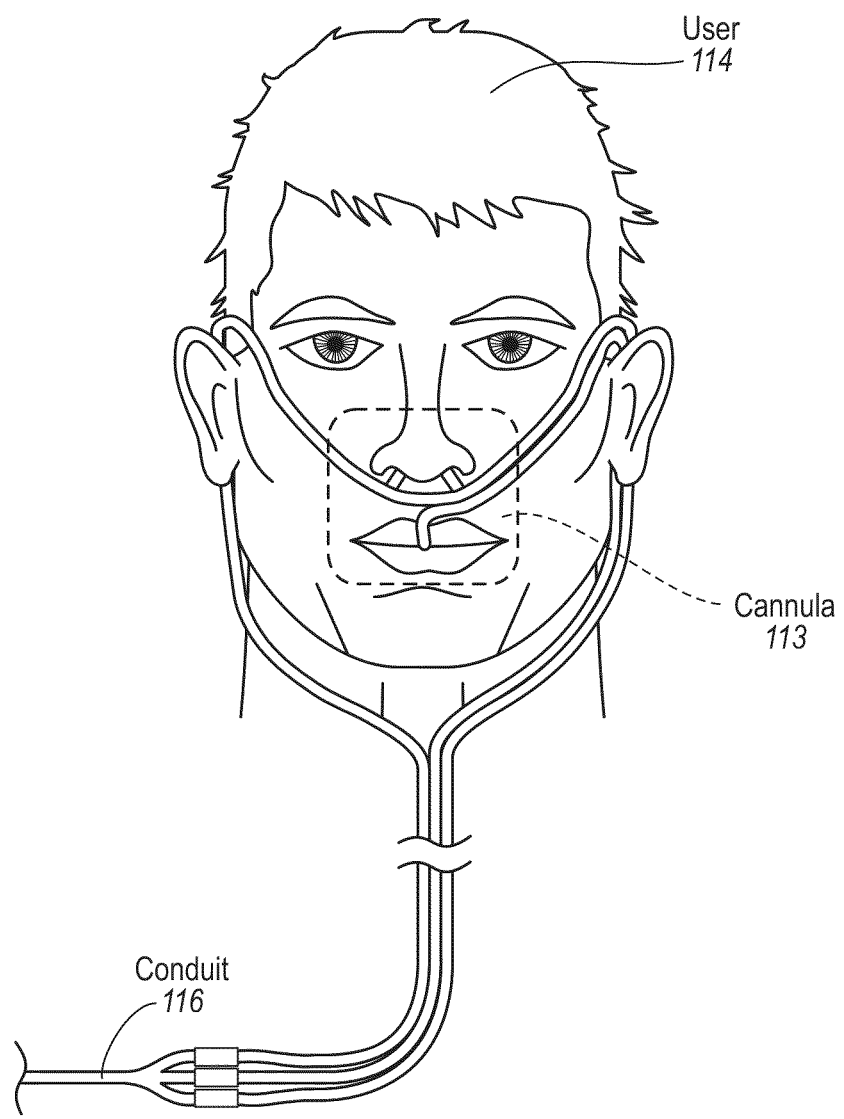

FIG. 1C depicts cannula 113. Cannula 113 can be hung over the ears of the user 114 to secure cannula 113 to the head of user 114. Conduit 116 can be connected to an oxygen supply such that oxygen can, when appropriate, flow into cannula 113 for inspiration by user 114.

Oxygen Delivery System

Generally, embodiments of the invention can include a microphone, such as, for example, a noise canceling electret condenser microphone. The microphone is utilized as a respiration sensor. The acoustical port of the microphone is connected to the pneumatic area of an oxygen delivery system (e.g., to a conduit for oxygen delivery). As such, pressure changes in the pneumatic area influence the diaphragm in the microphone.

The electrical port of the microphone is connected to an analog to digital converter ("ADC"). The ADC can be a separate circuit component or can be integrated into a microcontroller or microprocessor. The electrical signal of the microphone is sampled and digitized at an appropriate rate and the electrical signal converted to digital data. Accordingly, discrete signal processing techniques can be used to analyze the digital data. Signal conditioning and processing firmware then perform further processing (e.g., filtering) of the digital data. The digital data processing yields an internal (e.g., filtered) signal that corresponds to low frequency breathing events of a user.

Based on the internal signal, the microcontroller or microprocessor then controls a valve to allow oxygen to flow for an appropriate (e.g., predetermined and/or calculated) period of time and thus dispense an appropriate bolus (dose) of oxygen. The time period for the valve to remain open can be based on a combination of one or more of: the pressure/altitude at the location of the user, the respiration rate of the user, and the depth of inspiration of the user. In some embodiments, the time period for the vale to remain open is in a range from 10 milliseconds to 500 milliseconds.

The microphone's diaphragm can be configured to endure the relatively high pressure from the flow of oxygen and also to sense the (potentially relatively minute) pressure changes associated with breathing. At predetermined times, the microcontroller or microprocessor can also read barometric pressure from another transducer and convert this to a number representative of pressure altitude. The microcontroller or microprocessor can use the representative number to adjust oxygen flow to compensate for the pressure altitude.

Figure 2A:
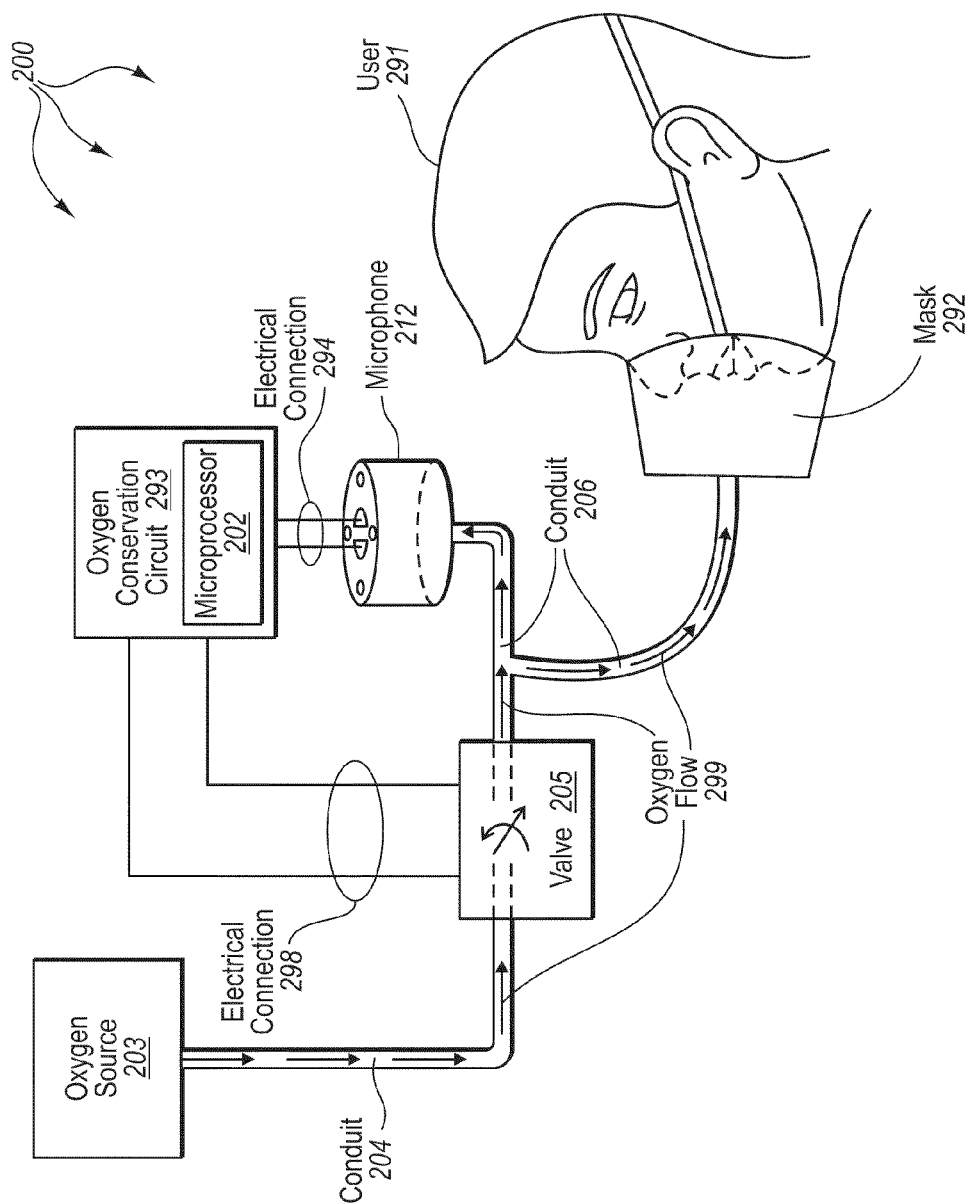
FIG. 2A illustrates an example oxygen delivery system.

Turning now to FIG. 2A, FIG. 2A illustrates an example oxygen delivery system 200. As depicted, oxygen delivery system 200 includes oxygen source 203 (e.g., an oxygen tank, an oxygen concentrator, a chemical oxygen generator, and an on board oxygen generator, etc.), valve 205 (a pneumatic valve), microphone 293, mask 292, user 291, and oxygen conservation circuit 293. Conduit 204 pneumatically connects oxygen source 203 and valve 205 to one another. Conduit 206 pneumatically connects valve 205, microphone 212, and mask 292 to one another. Electrical connection 298 electrically connects valve 205 and oxygen conservation circuit 293 to one another. Electrical connection 294 electrically connects microphone 212 and oxygen conservation circuit 293 to one another.

Valve 205 can be an electronically controlled valve having an open setting that permits oxygen flow 299 to pass from conduit 204 to conduit 206 and a closed setting that prevents oxygen flow 299 from passing from conduit 204 to conduit 206.

Microphone 212 can include a diaphragm and a transducer. Movement of the diaphragm can be influenced by sound in conduit 206, pressure changes in conduit 206, and user breathing at mask 292. Movement of the diaphragm results in a microphone signal having a sound component, a pneumatically induced noise component, and a user breathing component. The transducer within microphone 212 is configured to convert diaphragm movements into microphone output electrical signals. The microphone output electrical signals can be transferred over electrical connection 294 to oxygen conservation circuit 293.

Oxygen conservation circuit 293 can optionally include an analog filter. The analog filter can be configured to filter (potentially significant portions) of sound components and at least some of the pneumatically induced noise component. Thus, an analog filter can be used to at least partially reduce sound components and pneumatically induced noise components in the output electrical signals prior to sending the output electrical signals to microprocessor 202. Thus, embodiments of the invention can include an analog filer that partial filters signals before delivery to a microprocessor. The microprocessor can then further process received signals as appropriate to detect breathing cycle events.

Generally, microprocessor 202 is configured to regulate the delivery of oxygen to user 291 based on a (potentially filtered) output electrical signal received from microphone 212. From a (potentially filtered) output electrical signal, microprocessor 202 (and other components of oxygen conservation circuit 293) controls valve 205 to regulate the flow oxygen between conduit 204 and conduit 206. For example, microprocessor 202 and other components of oxygen conservation circuit 293 can interoperate to transition valve 205 from a closed setting to an open setting and vice versa. Oxygen conserving circuit 293 can send electrical signals to valve 205 over electrical connection 298 to control valve 205. The electronic signals can transition valve 205 from a closed setting to an open setting, cause valve 205 to maintain an open setting, transition valve 205 from an open setting to a closed setting, or cause valve 205 to maintain a closed setting.

Microprocessor 202 can include an ADC for converting a (potentially filtered) output electrical signal to digital data. Microprocessor 202 can run various algorithms on the digital data to further filter the digital data and differentiate what portion of the breathing cycle user 291 is currently in. For example, microprocessor 202 can differentiate between an inspiration event and other portions of the breathing cycle (e.g., an expiration event, resting between, etc.). When microprocessor 202 determines that a signal is indicative of an inspiration event, valve 205 is transitioned to the open setting. Thus, oxygen is permitted to flow from conduit 204 to conduit 206 when user 291 is inspiring to delivery an appropriate bolus of oxygen. When microprocessor 202 determines that delivery of a bolus of oxygen is complete valve 205 is transitioned to the closed setting or kept in a closed condition. Thus, oxygen is conserved when user 291 is in other portions of the breathing cycle (i.e., when user 291 is not inspiring).

Oxygen Conserving Circuit

Figure 2B:
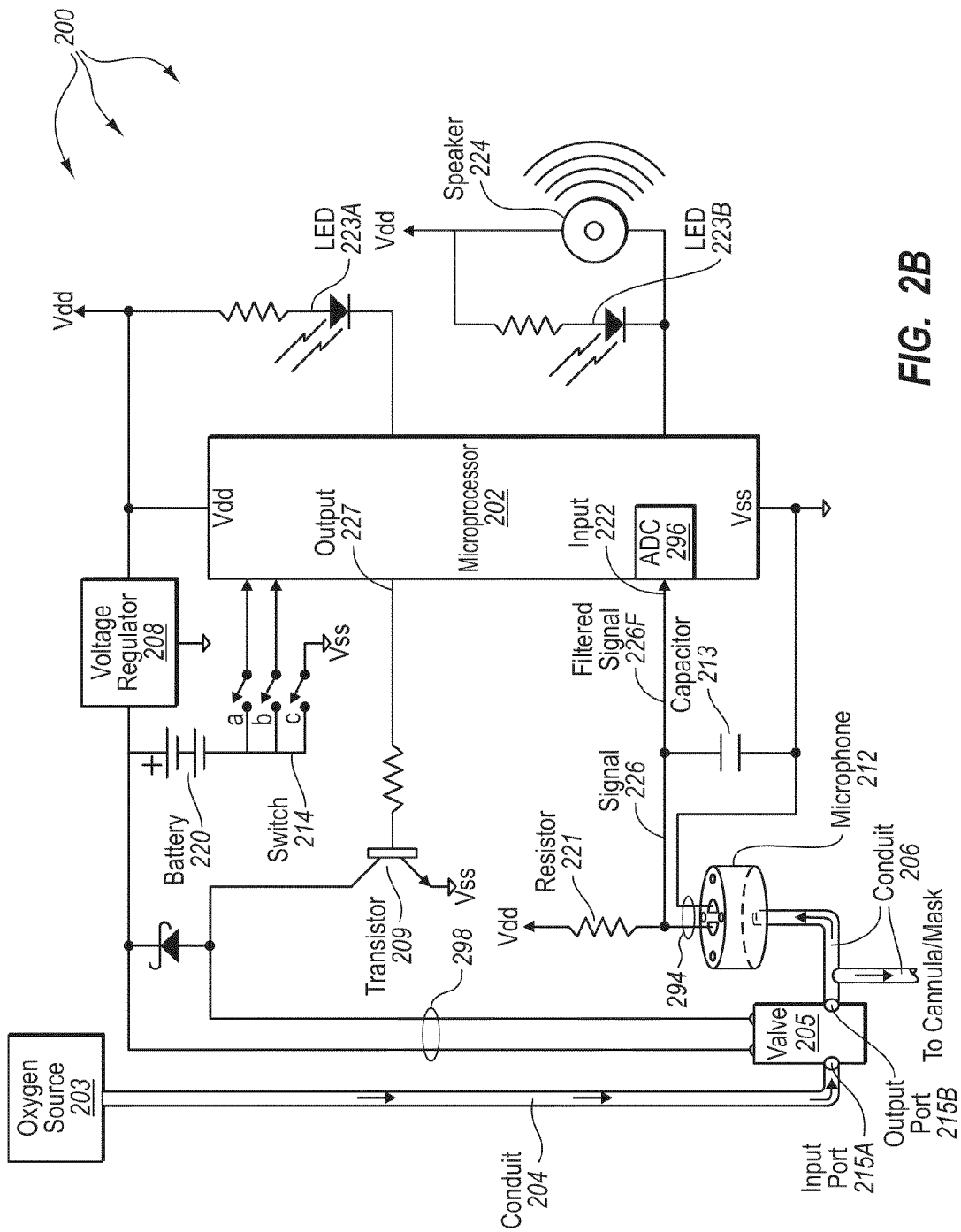
FIG. 2B illustrates the example oxygen delivery system with a more detailed view of an oxygen conservation circuit.

FIG. 2B illustrates the oxygen delivery system 200 with a more detailed view of oxygen conservation circuit 293. Oxygen conservation circuit 293 can be used to conserve oxygen of oxygen source 203. As depicted, valve 205 includes input port 215A and output port 215B. In some embodiments, valve 205 is a normally-closed pneumatic valve including input port 215A and output port 215B. Conduit 204 pneumatically connects oxygen source 203 and input port 215A to one another. Conduit 206 pneumatically connects output port 215B and microphone 212 to one another. As such, (even relatively small) changes in pressure within conduit 206 can influence the diaphragm of microphone 212.

Within oxygen conservation circuit 293, resistor 221 (e.g., 10 KΩ) is used to apply a small operating current to microphone 212. Signal 226 is an output electrical signal from microphone 212 that corresponds to the changes in (e.g., the micro) pressure placed on the diaphragm of microphone 212. Capacitor 213 places a (e.g., relatively) large first order low-pass filter on signal 226 resulting in filtered signal 226F, or a filtered output electrical signal from microphone 212.

Filtered signal 226F is applied as input 222 to ADC 296. ADC 296 converts filtered signal 226F into digital data representing filtered signal 226F.

Firmware in microprocessor 202 processes the digital data to further filter the digital data and differentiate between different portions of the breathing cycle for user 291. When inspiration is detected from the digital data, signal can be sent at output 227 to transition valve 205 to an open setting via buffer transistor 209

Control switch 214 facilitates a way to provide various user-controlled settings, if the application calls for such. Battery 220 powers valve 205 and microprocessor 202 through voltage regulator 208. LED 223A (e.g., a green LED) and LED 223B (e.g., a red LED) can be included in oxygen conservation circuit 293 to provide a visual indication to inform a user of warnings, alerts, and alarms. Likewise, speaker 224 can be included in oxygen conservation circuit 293 to provide an audible indication to inform a user of warnings, alerts, and alarm.

Accordingly, embodiments of the invention include a microphone, appropriate electrical components, and a microcontroller interconnected to differentiate portions of the breathing cycle of a human and control the dispensing of oxygen. Other embodiments of the invention can discern the breathing cycles of a human and control the dispensing of oxygen using discreet analog circuitry, a custom integrated circuit, a microprocessor, or any combination of these or other components.

Microprocessor Components and Logic

Figure 2C:
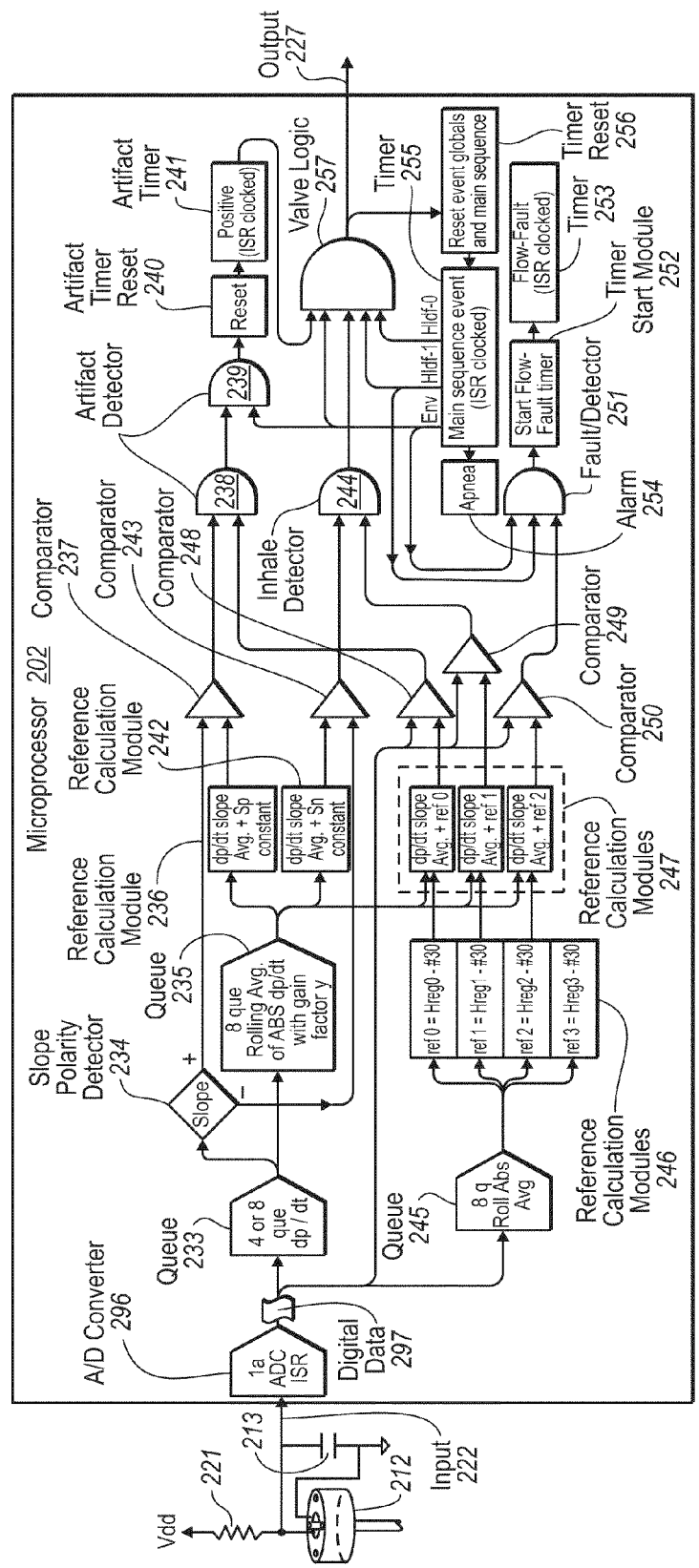
FIG. 2C illustrates internal components and logic of a microprocessor for differentiating between different portions of a breathing cycle.

FIG. 2C illustrates internal components and logic of microprocessor 202. As depicted, ADC 296 converts filtered signal 226F to digital data 297. Digital data 297 essentially represents the breathing component of the output electrical signal from microphone 212. For example, ADC 296 can sample filtered signal 226F and convert filtered signal 226F to digital data 297. The sample rate can be consistent at one sample per time period, where the time period is selected in a range from 64 us to 8 ms, such as, for example, 512 us. An appropriate sample rate is one which gives a resolution in time to sufficiently monitor a user's breathing, control the valve, and monitor the dispensing of oxygen. In some embodiments, an 8-bit conversion result is sufficient for calculations that will be done on this data. Fewer or more bits can be used as desired.

A subset of samples from ADC 296 (i.e., of digital data 297) can be stored in queue 233. The frequency of samples stored in queue 233 can range from every one to 1 out of 256 ADC. In some embodiments, a range from 2 to 32 samples are stored in queue 233, of which all or some subset are used. For example, when 16 samples are stored, 4 samples may be used. With the insertion of each new sample, the oldest entry is dropped. Each new sample can be compared to the oldest entry to calculate the slope of the signal from microphone 212.

The slope determined from data in queue 233 can be forwarded to slope polarity detector 234. Slope polarity detector 234 can determine if the slope of the signal from microphone 212 is positive or negative. A negative slope can indicate a change in pressure in conduit 206 representative of the start of inspiration. A positive slope can indicate expiration, the valve opening, or some noise. As such, a positive slope is used to trigger additional logic to test for any of these conditions to prevent false trips in the system and to monitor system functionality.

Queue 235 can store the absolute values of slope values. The absolute values for slope values stored in queue 235 can be used to calculate the rolling average of the absolute value of the slope. Slope absolute values can be used to determine the magnitude of the activity coming from the microphone. Every value of the slope from queue 233 can be used, but is not required. For example, every 1 out of 2 to 1 out of 8 of the values from queue 233 is processed and inserted into queue 235. With the insertion of each new sample, the last sample is dropped and the average of the current set of samples is calculated. A gain factor may be used to scale the average value into a more usable range for additional calculations later.

Reference calculation module 236 can receive slope absolute values generated from data in queue 235. Reference calculation module 236 can calculate a reference from the rolling average of slope absolute values and possibly also a constant. The reference can be calculated by adding an offset to the rolling average of the slope absolute from queue 235. The calculated reference can be used for positive artifact detection, such as, for example, to detect expiration or noise, and to prevent negative pressure changes from appearing to be inspiration.

Reference calculation module 242 can receive slope absolute values generated from data in queue 235. Reference calculation module 242 can calculate a rolling average of slope absolute values and a constant used for inspiration detection. For example, the rolling average of absolute slope value can be added to a constant to provide a threshold for breath detection.

Queue 245 receives and stores samples from ADC 296. Data in queue 245 can be used to calculate a rolling average of sensor calculations. Queue 245 can store from 1 out of 8 to 1 out of 256 samples from ADC 296. With the insertion of each new sample, the last sample is dropped and the average of the current set of samples is calculated. The slower data rate of this queue prevents the average from changing too quickly. This average is used to generate many reference values for other comparisons.

Reference calculation modules 246 receive rolling averages generated from data in queue 245. Reference calculation modules can calculate references based on the rolling averages. Predetermined values can be combined with rolling averages to create references for use in detecting various operating conditions.

Reference calculation modules 247 calculate references based on references from reference calculation modules 246 and absolute slope values calculated from data in queue 235. For example, the rolling average of slope absolute value can be combined with references from reference calculation modules 246 to generate comparison values to detect various operating conditions.

Comparator 237 receives slope polarities from slope polarity detector 234 and the reference from reference calculation module 236. Comparator 237 compares the magnitude of the slope of a current sample (from queue 235) that has positive slope to the reference from reference calculation module 236. Any time the magnitude of the slope of a current sample with positive slope is greater than the reference, a positive artifact may be present.

Comparator 243 receives slope polarities from slope polarity detector 234 and the reference from reference calculation module 242. Comparator 2243 compares the magnitude of the slope of a current sample (from queue 235) that has negative slope to the reference from reference calculation module 242. When the magnitude of the negative slope is greater than the reference, there is an increased likelihood that a breathing cycle has been detected at the start of inspiration.

Comparator 248 receives samples from ADC 296 and a comparison value from reference calculation modules 247. Comparator 248 can determine if an incoming signal is in a range of values sufficient to allow the detection of Positive Artifacts.

Comparator 249 receives samples from ADC 296 and a comparison value from reference calculation modules 247. Comparator 249 can determine if an incoming signal is in a range of values sufficient to allow the detection of breath inspiration.

Comparator 250 receives samples from ADC 296 and a comparison value from reference calculation modules 247. Comparator 250 can determine if an incoming signal is in a range of values sufficient to allow the detection of a valve open condition at valve 205.

Artifact detector 238 receives input from comparator 237 and from comparator 248. When the comparison for a positive artifact (at comparator 237) determines that a positive artifact may be present, the result is gated with a comparison of the absolute reading to determine the certainty of the presence of a positive artifact.

Inhale detector 244 receives input from comparator 243 and from comparator 249. When what appears to be the start of inspiration is detected, the detection is gated with an indication if an incoming signal is in range of values sufficient to detect inspiration. If the level of the microphone signal is not in the proper range, what was detected as a breathing cycle may actually be detected noise. If the level of the microphone signal is in the proper range, then there is increased likelihood of appropriately detected inspiration (e.g., at the start of a breathing cycle).

Artifact detector 239 receives input from artifact detector 238 and from timer 255. When a user is in a normal breathing cycle, or envelope, then the results of positive artifact detection (from artifact detector 238) are to be ignored, otherwise a positive artifact can be processed when detected.

Artifact timer reset 240 receives input from artifact detector 239. When a positive artifact has been detected, normal breath detection is stopped for a small amount of time, such as, for example, 1 ms-50 ms. Artifact timer reset 240, loads artifact timer 241 with the amount of time. The amount of time may vary according to the magnitude of the slope that triggered this event.

Artifact timer 241 decrements with each pass through ISR. When timer 241 reaches zero, normal operation (e.g. breath detection) is resumed.

Timer 255 is the main event timer. Timer 255 is incremented on every interrupt, and is used to generate signals representing the breathing envelope and other internal timing.

Fault detector 251 receives input from comparator 250 and from various outputs of timer 255. The logic of fault detector 251 combines various timer and detection signals to control the flow fault alarm sequence.

Timer start module 252 receives input from fault detector 251. When a flow fault alarm is detected, timer start module 252 can start timer 253. Timer start module 252 can also active visual indicators (e.g., LED 223A and/or 223B) and/or audio indicators (e.g., speaker 224) to alert a user to a flow fault condition. A flow fault condition indicates that oxygen is not flowing between conduits 204 and 206 during inspiration.

Flow fault timer 253 can be a unique timer or integrated with the main event timer. Flow fault timer 253 is used to control the flow fault alarm, such as, for example, determine how long the flow fault alarm is active.

Apnea alarm 254 receives input from timer 255. Apnea alarm 254 can be initiated when no valid inspiration event has been detected for a predetermined time period. Audio and/or visual signals can be used to alert the user to the apnea condition.

Timer reset 256 is configured to reset timer 255 (e.g., to zero) at the start of a valid inspiration detection. Timer 255 continues to count up and is compared to several timing parameters to control the sequence of system events.

Valve logic 257 receives input from inhale detector 244, from artifact timer 241, and from various outputs of timer 255. Thus, when appropriate events and conditions are met, valve 205 is transitioned to an open setting so that oxygen can flow from conduit 204 to conduit 206 to deliver a desired bolus of oxygen. A desired bolus of oxygen can be configured based on one or more of: the pressure/altitude at the location of the user, the respiration rate of the user, and the depth of inspiration of the user.

Valve logic 257 can send output 227 to driver transistor 209 to cause transistor 209 to transition valve 205. Valve logic 257 can consider a variety of conditions and events, including whether a breathing envelope or a positive artifact timeout is currently active, or if a valid inspiration event has been detected. Valve 205 can then be controlled by additional logic to regulate the desired bolus. The bolus may be adjusted by changing the open duration of valve 205 or by modulating power to the valve, thus controlling the volume allowed to flow through the valve, or by some other means.

Thus, generally as a user starts to inspire, the pressure in conduit 206 starts to decrease. The decrease in pressure is measured as a negative slope indicative of inspiration and a bolus of oxygen is delivered to a user.

Breathing Pattern Detection

In some embodiments, the detection of breathing patterns in the signal from the microphone involves many steps. After most of the audio portion is removed, the signal can still contain many noise components in addition to the breathing component. The filtering for separating the breathing from the noise can include setting reference points based upon the average of the signal and the average of the absolute value of the slope of the signal. If the current value of the signal is much higher than the average value of the signal, then there is an increased likelihood that the current value is not in the correct range of values, and should not be used to detect breathing. On the other hand, that type of signal would be more indicative of the high-pressure burst associated with the dispensing of oxygen to the user than with any portion of the user's breathing.

Shaking the outlet tubing induces another type of noise into the signal. This more rhythmic noise shows itself in constant changes in the slope of the signal. By adjusting the references based upon the absolute value of the slope of the signal, these periods of high noise can adjust the references towards requiring a stronger breathing signal to trip the inhale detection. These and other types of adjustment to the references can reduce the possibility of dispensing oxygen erroneously during periods of shaking, vibration, or turbulence.

In some embodiments, these adjustments are implemented using analog circuitry, such as, for example, a custom integrated circuit or ASIC, or with a program running on a microprocessor or microcontroller. In other embodiments, these adjustments are implement using a small amount of analog circuitry to filter out the higher frequency audio component and with the rest of the filtering and detection accomplished in a microcontroller.

Breathing Cycle Plots

Figure 3A:
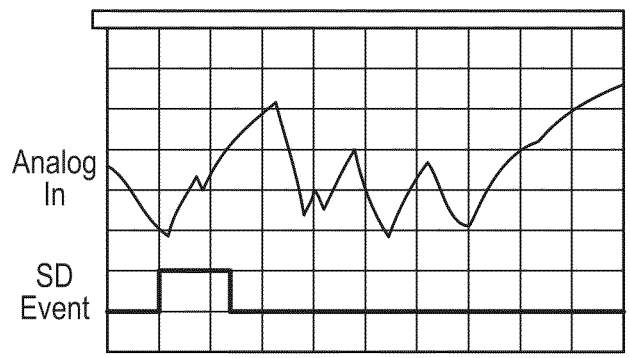
FIG. 3A depicts a plot of a breathing cycle with oxygen delivery.

FIG. 3A depicts a plot 301 of a breathing cycle with oxygen delivery. At the start of inspiration, the signal voltage drops. If the Analog In signal is falling with a rate of change that is of sufficiently large magnitude, an inspiration event will be triggered. The inspiration event, in turn will cause valve 205 to open allowing oxygen to flow. The oxygen flow will cause the pressure in conduit 206 to increase to a pressure larger than normal breathing pressure.

Valve 205 can be left on for an amount of time determined by several factors such as pressure altitude, user selected setting, user breathing patterns, etc. Once the valve has been turned off, the pressure can drop back to the normal breathing pressures, which at this point should still be in inspiration mode. Some noise may appear in the voltage signal as the result of the pneumatic pressure wave reflecting in the tubing, manifold, and valve. Expiration can then be recognized by a steady increase in pressure that takes the Analog In voltage signal back to a level near or slightly above the resting level.

Figure 3B:
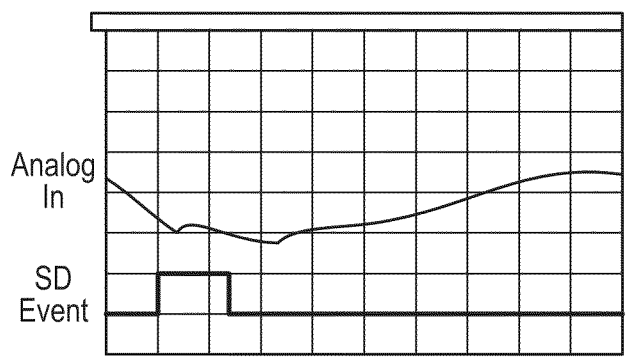
FIG. 3B depicts a plot of a breathing cycle without oxygen delivery.

FIG. 3B depicts a plot of a breathing cycle 302 without oxygen delivery. At the start of inspiration, the signal voltage drops. If the Analog In signal is falling with a rate of change that is of sufficiently large magnitude, an inspiration event can be triggered. The inspiration event in turn causes valve 205 to allow oxygen to flow. If there is a fault that keeps the valve from opening, or the oxygen supply is empty or blocked, no oxygen flows. In absence of the pressure burst from the oxygen supply in conduit 206, the Analog In signal will track the respiration cycle pressures. Expiration is recognized by a steady increase in pressure that takes the Analog In voltage signal back to a resting level. Microprocessor 202 can recognize this fault condition and alert the user with various audible and visible alarms.

Figure 3C:
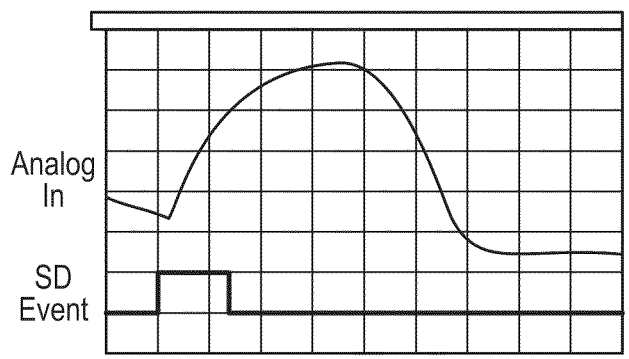
FIG. 3C depicts a plot of a breathing cycle with oxygen delivery with a restriction on the outlet side of the system.

FIG. 3C depicts a plot 303 of a breathing cycle with oxygen delivery with a restriction on the outlet side of the system. At the start of inspiration, the signal voltage drops. If the Analog In signal is falling with a rate of change that is of sufficiently large magnitude, an inspiration event is triggered. The inspiration event in turn causes valve 205 to allow oxygen to flow. The oxygen flow causes the pressure in conduit 206 to increase to a pressure much larger than normal breathing pressures. However, with a restriction in the outlet (e.g., a blockage in conduit 206 or cannula or mask connected to conduit 206), the pressure can increase to approximately match the oxygen supply pressure. Microprocessor 202 can recognize this fault condition and alert the user with various audible and visible alarms.

Figure 4:
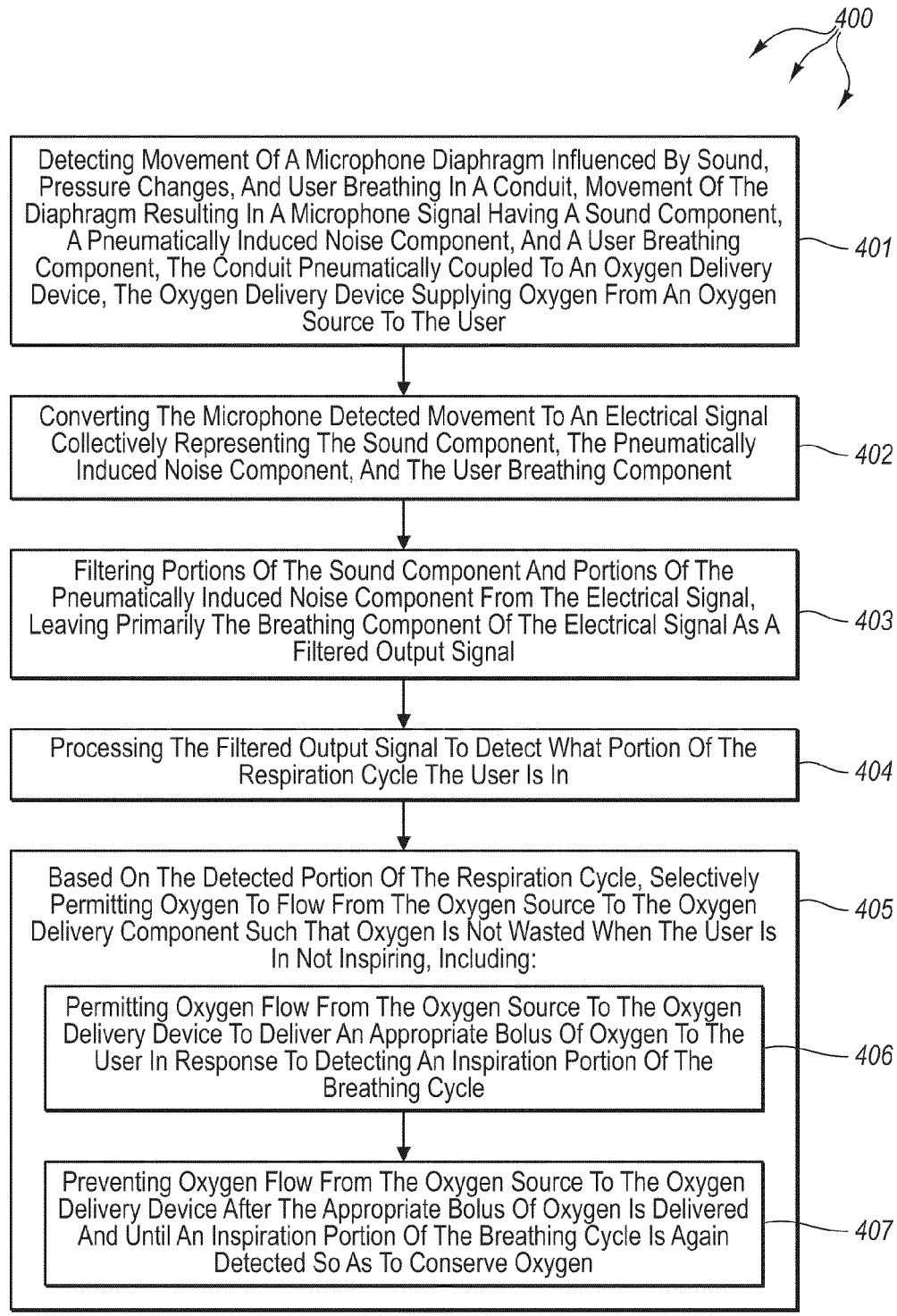
FIG. 4 illustrates an example flow chart of a method for regulating oxygen flow in an oxygen delivery system.

Embodiments of the invention include methods for regulating oxygen flow in an oxygen delivery system. For example, FIG. 4 illustrates an example flow chart of a method 400 for regulating oxygen flow in an oxygen delivery system. The method 400 will be described with respect to the components and data of oxygen delivery system 200.

Method 400 includes an act of detecting movement of a microphone diaphragm, the microphone diaphragm influenced by sound, pressure changes, and user breathing in a conduit, movement of the diaphragm resulting in a microphone signal having a sound component, a pneumatically induced noise component, and a user breathing component, the conduit pneumatically coupled to an oxygen delivery device, the oxygen delivery device supplying oxygen from an oxygen source to the user (act 401). For example, movement of the diaphragm in microphone 212 can be detected. Movement of the diaphragm can be influenced by sound and pressure changes conduit 206 as well as by user 291 breathing into mask 292. Movement of the diaphragm results in an electrical signal from microphone 212, having a sound component, a pneumatically induced noise component, and a breathing component cause by user 291.

Method 400 includes an act of converting microphone signal, an electrical signal collectively representing the sound component, the pneumatically induced noise component, and the user breathing component (act 402). For example, microphone 202 can convert the acoustic signal to signal 226. Signal 226 can collectively represent the sound component, the pneumatically induced noise component, and the user breathing component in the acoustic signal.

Method 400 includes an act of filtering portions of the sound component and portions of the pneumatically induced noise component from the electrical signal, leaving primarily the breathing component of the electrical signal as a filtered output electrical signal (act 403). For example, capacitor 213 can be used to filter signal 226 to remove portions of the sound component and pneumatically induced noise component from signal 226. Filtering signal 226 results in filtered signal 226F including primarily the breathing component of electrical signal 226.

Method 400 includes an act of processing the filtered output electrical signal to detect what portion of the respiration cycle the user is in (act 404). For example, microprocessor 202 can execute logic (similar to that depicted in FIG. 2C) to determine what portion of the respiration cycle user 291 is in, such as, for example, inspiration, expiration, or resting between.

Method 400 includes an act of selectively permitting oxygen to flow from the oxygen source to the oxygen delivery component (act 405). For example, based on what portion of the respiration cycle user 291 is detected to be in, microprocessor 202 and transistor 209 can interoperate to selectively permit oxygen to flow from oxygen source 203 to mask 292.

Method 400 includes an act of permitting oxygen to flow from the oxygen source to the oxygen delivery device when the filtered output electronic signal is indicative of an inspiration event (act 406). For example, microprocessor 202 and transistor 209 can interoperate to cause valve 205 to transition to an open setting permitting oxygen flow 299 to pass from conduit 204 to conduit 206. Method 400 includes an act of preventing oxygen from flowing from the oxygen source to the oxygen delivery device when filtered output electronic signal is indicative of a portion of the breathing cycle other than an inspiration event such that oxygen is not wasted when the user is in not inspiring (act 407). For example, microprocessor and transistor 209 can interoperate to cause valve 205 to transition to a closed setting preventing oxygen flow 299 from passing from conduit 204 to conduit 206.

Accordingly, embodiments of the invention use a microphone to detect breathing sounds indicative of different portions of a breathing cycle. Sounds not related to the breathing cycle are filtered out of the signal. Using the breathing sounds, a microprocessor differentiates inspiration from other portions of the breathing cycle. When inspiration is detected, a valve is transitioned to permit the flow of oxygen from an oxygen source to a user. The microprocessor can also detect fault conditions, such as, for example, failure to deliver a bolus of oxygen and restrictions in the flow of oxygen from the oxygen source to a user.

Embodiments of the present invention may comprise or utilize a special purpose or general-purpose computer including computer hardware, as discussed in greater detail below. Embodiments within the scope of the present invention also include physical and other computer-readable media for carrying or storing computer-executable instructions and/or data structures. Such computer-readable media can be any available media that can be accessed by a general purpose or special purpose computer system. Computer-readable media that store computer-executable instructions are physical storage media. Computer-readable media that carry computer-executable instructions are transmission media. Thus, by way of example, and not limitation, embodiments of the invention can comprise at least two distinctly different kinds of computer-readable media: physical storage media and transmission media.

Physical storage media includes RAM, ROM, EEPROM, FLASH, CD-ROM or other optical disk storage, magnetic disk storage or other magnetic storage devices, or any other medium which can be used to store desired program code means in the form of computer-executable instructions or data structures and which can be accessed by a general purpose or special purpose computer.

With this description and following claims, a "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer properly views the connection as a transmission medium. Transmissions media can include a network and/or data links which can be used to carry or desired program code means in the form of computer-executable instructions or data structures and which can be accessed by a general purpose or special purpose computer. Combinations of the above should also be included within the scope of computer-readable media.

Further, it should be understood, that upon reaching various computer system components, program code means in the form of computer-executable instructions or data structures can be transferred automatically from transmission media to physical storage media (or vice versa). For example, computer-executable instructions or data link can be buffered in RAM within a network interface module (e.g., a "NIC"), and then eventually transferred to computer system RAM and/or to less volatile physical storage media at a computer system. Thus, it should be understood that physical storage media can be included in computer system components that also (or even primarily) utilize transmission media.

Computer-executable instructions comprise, for example, instructions and data which cause a general purpose computer, special purpose computer, or special purpose processing device to perform a certain function or group of functions. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the invention may be practiced in network computing environments with many types of computer system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, pagers, routers, switches, and the like. The invention may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Components can be connected to one another over a system bus and/or over (or be part of) a network, such as, for example, a Local Area Network ("LAN"), a Wide Area Network ("WAN"), and even the Internet. Accordingly, each of the depicted components as well as any other connected components, can create message related data and exchange message related data (e.g., Internet Protocol ("IP") datagrams and other higher layer protocols that utilize IP datagrams, such as, Transmission Control Protocol ("TCP"), Hypertext Transfer Protocol ("HTTP"), Simple Mail Transfer Protocol ("SMTP"), etc.) over the network.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An oxygen delivery system operative to regulate a flow of oxygen during an inspiration event of a respiratory cycle, and comprising:
    an oxygen source;
    a first portion of a conduit pneumatically coupling the oxygen source to a first port of an electronically controlled valve;
    a second portion of the conduit pneumatically coupling the electronically controlled valve to an oxygen output device and to a microphone;
    wherein the electronically controlled valve has at least an open setting that permits the flow of oxygen from the first port to the second port and having at least a closed setting that prevents the flow of oxygen from the first port to a second port;

wherein the microphone is configured with a diaphragm and a transducer, movement of the diaphragm influenced by audible sound in the second portion of conduit, pneumatically induced noise in the second portion of the conduit, and pressure changes associated with user breathing at the oxygen output device, movement of the diaphragm resulting in a microphone signal having a sound component corresponding to the audible sound, a pneumatically induced noise component corresponding to the pneumatically induced noise, and a user breathing component corresponding to the pressure changes associated with user breathing, the transducer configured to convert diaphragm movements into microphone output electrical signals;

a microcontroller electrically connected to the microphone, the microcontroller for regulating operation of the oxygen delivery system so as to conserve oxygen, wherein the microcontroller is also electrically connected to a valve assembly that controls the electronically controlled valve via an electrical connection, the microcontroller configured to indicate to the valve assembly when the electronically controlled valve is to transition from the closed setting to the open setting, when the electronically controlled valve is to maintain the open setting, when the electronically controlled valve is to transition from an open setting to a closed setting, and when the electronically controlled valve is to maintain the closed setting, the microcontroller further configured to:

receive output electrical signals from the microphone;

filter out portions of the sound component and portions of the pneumatically induced noise component from received microphone output electrical signals, leaving primarily the breathing component of the microphone output electrical signals as a filtered output signal;

determine when the filtered output signal is indicative of an inspiration event such that the electronically controlled valve can be transitioned to the open setting to deliver a specified bolus of oxygen; and determine when delivery of the specified bolus of oxygen is complete such that the electronically controlled valve can be transitioned to the closed setting.

2. The system as recited in claim 1, wherein the oxygen source comprises one or more of: an oxygen tank, an oxygen concentrator, a chemical oxygen generator, and an on board oxygen generator.

3. The system as recited in claim 1, wherein the microphone comprises a noise canceling electret condenser microphone.

4. The system as recited in claim 1, wherein the valve comprises a pneumatic valve.

5. The system as recited in claim 1, wherein the valve assembly is a driver transistor that drives the valve.

6. The system as recited in claim 1, further comprising indicators for indicating a fault in the delivery of oxygen.

7. The system as recited in claim 1, further comprising a battery for powering the microcontroller and the valve.

8. The system as recited in claim 1, further comprising:
an analog filter situated electrically between the microphone and the microcontroller;
a first other electrical connection connecting the microphone to an analog filter;
a second other electrical connection connecting the analog filter to the microcontroller;
wherein the analog filter is configured to:

receive microphone output electrical signals from the microphone over the first other electrical connection;
filter out at least some portions of the sound component and portions of the pneumatically induced noise component from the microphone output electrical signal to reduce the portions of the sound component and pneumatically induced noise component remaining in the output electrical signals; and
send output electrical signals with reduced sound components and reduced pneumatically induced noise components to the microcontroller over the second other electrical connection.

9. A circuit for regulating the flow of oxygen in an oxygen deliver system, the circuit comprising:
an electrical connection to a microphone, the electrical connection for receiving an electrical signal from the microphone, the electrical signal representing detected audible sounds, detected pneumatically induced noise, and detected pressure changes associated with user breathing in a conduit used to deliver oxygen to a user, the electrical signal including a sound component corresponding the detected audible sounds, a pneumatically induced noise component corresponding to the detected pneumatically induced noise, and a user breathing component corresponding to the detected pressure changes associated with user breathing;
a microcontroller, the microcontroller including:
an input port for receiving the output electrical signal;
an analog to digital converter for converting the output electrical signal to digital data;
a filter for filtering out portions of the sound component and portions of the pneumatically induced noise component from the digital data, leaving primarily the breathing component of the microphone output electrical signal as a filtered digital data signal;
logic for determining when an inspiration portion of the breathing cycle is represented in the filtered digital data and for activating a signal indicating that a bolus of oxygen is to be delivered from an oxygen source; and
an output port for sending the signal indicating that the bolus of oxygen is to be delivered from the oxygen source; and
a transistor connected to the output port, the transistor configured to receive signals sent from the output port and cause a valve to transition from a closed setting to an open setting to deliver a bolus of oxygen for the oxygen source in response to receiving a signal indicating that a bolus of oxygen is to be delivered.

10. The circuit as recited in claim 9, wherein the microcontroller further comprises logic for detecting an apnea condition in a user.

11. The circuit as recited in claim 9, wherein the microcontroller further comprises logic for detecting faults in the delivery of oxygen to the user from the digital data.

12. The circuit as recited in claim 11, wherein the logic for detecting faults in the delivery of oxygen to a user comprises logic for detecting a failure to deliver a bolus of oxygen from an oxygen source to the user during and in response to a detected inspiration portion of a breathing cycle.

13. The circuit as recited in claim 11, wherein the logic for detecting faults in the delivery of oxygen to a user comprises logic for detecting that the flow of oxygen in a conduit between the oxygen source and the user is restricted.

14. The circuit as recited in claim 11, further comprising visual indicator components for visually indicating when a fault in the delivery of oxygen is detected.

15. The circuit as recited in claim 11, further comprising audio indicator components for audibly indicating when a fault in the delivery of oxygen is detected.

16. The circuit as recited in claim 9, wherein the microcontroller further comprises logic for detecting positive artifacts indicative of the delivery of a bolus of oxygen to the user from the digital data.

17. A method for supplying oxygen to a user's respiratory system during a respiration cycle that includes inspiration, the method comprising
- detecting movement of a microphone diaphragm influenced by audible sound, noise, and pressure changes, in a conduit, movement of the diaphragm resulting in a microphone signal having a sound component corresponding to the audible sound, noise component corresponding to the noise, and a user breathing component corresponding to pressure changes associated with user breathing, the conduit pneumatically coupled to an oxygen delivery device, the oxygen delivery device supplying oxygen from an oxygen source to the user;
- converting microphone detected movement to an electrical signal collectively representing the sound component, the noise component, and the user breathing component;
- filtering out portions of the sound component and portions of the noise component from the electrical signal, leaving primarily the breathing component of the electrical signal as a filtered output signal;
- processing the filtered output signal to detect what portion of the respiration cycle the user is in;
- based on the detected portion of the respiration cycle, selectively permitting oxygen to flow from the oxygen source to the oxygen delivery device, including:
  - permitting oxygen flow from the oxygen source to the oxygen delivery device to deliver an appropriate bolus of oxygen to the user in response to detecting an inspiration portion of the breathing cycle; and
  - preventing oxygen flow from the oxygen source to the oxygen delivery device after the appropriate bolus of oxygen is delivered and until an inspiration portion of the breathing cycle is again detected so as to conserve oxygen.

18. The method as recited in claim 17, wherein the act of processing the filtered output electrical signal to detect what portion of the respiration cycle the user is in comprises an act of determining the polarity of the slope of the microphone signal.

19. The method as recited in claim 17, wherein the act of permitting oxygen to flow from the oxygen source to the oxygen delivery device comprises an act of transitioning a valve between the oxygen source and the oxygen delivery device to an open setting for a specified period of time based on one or more of: a pressure/altitude at the location of the user, a respiration rate of the user, and a depth of inspiration of the user.

20. The method as recited in claim 19, wherein the act of transitioning a valve between the oxygen source and the oxygen delivery device to the open setting for a specified period of time comprises an act of transitioning a valve between the oxygen source and the oxygen delivery device to the open setting for a specified period of time, wherein the specified period of time is selected from a specified period of time in a range from 10 milliseconds to 500 milliseconds.

21. The system as recited in claim 1, wherein the filtered output signal corresponds to low frequency breathing events of the user.

* * * * *